US012797042B2

(12) United States Patent

Tanaka et al.

(10) Patent No.: US 12,797,042 B2

(45) Date of Patent: Nov. 17, 2026

(54) ULTRASOUND DIAGNOSTIC APPARATUS AND PROGRAM

(71) Applicant: FUJIFILM Corporation, Tokyo (JP)

(72) Inventors: Chizue Tanaka, Tokyo (JP); Nobuhiko Fujii, Tokyo (JP); Yuko Sato, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/029,081

(22) Filed: Jan. 17, 2025

(65) Prior Publication Data

US 2025/0248692 A1 Aug. 7, 2025

(30) Foreign Application Priority Data

Feb. 1, 2024 (JP) ................................. 2024-014475

(51) Int. Cl.
*A61B 8/00* (2006.01)
*G06T 7/00* (2017.01)

(52) U.S. Cl.
CPC ............ *A61B 8/5215* (2013.01); *A61B 8/461* (2013.01); *G06T 7/0012* (2013.01); *G06T 2207/10132* (2013.01)

(58) Field of Classification Search
CPC ......... A61B 8/5215; A61B 8/461; A61B 8/54; A61B 8/46; G06T 7/0012; G06T 2207/10132
See application file for complete search history.

(56) References Cited

U.S. PATENT DOCUMENTS 9,157,894 B2 * 10/2015 Jiang ........................ A61B 8/08
11,593,933 B2 * 2/2023 Shriram .................... G06T 7/73
2003/0174890 A1 * 9/2003 Yamauchi ............ A61B 5/1075 382/199
2010/0305441 A1 * 12/2010 Lin ......................... A61B 8/14 600/443
2013/0150721 A1 * 6/2013 Kawabata ............ A61B 8/4488 600/447
2020/0411165 A1 * 12/2020 Torii ...................... G16H 30/20
2021/0065365 A1 * 3/2021 Odagiri ..................... G06T 7/70
2021/0311424 A1 * 10/2021 Mori ...................... G03G 15/55
2024/0046423 A1 * 2/2024 Maruyama ................ G06T 5/70
2024/0320833 A1 * 9/2024 Han ...................... G06T 7/0002

FOREIGN PATENT DOCUMENTS

JP H05-253220 A 10/1993
JP 2010-274111 A 12/2010

* cited by examiner

*Primary Examiner* — Baisakhi Roy

(74) *Attorney, Agent, or Firm* — Studebaker Brackett PLLC

(57) ABSTRACT

An image quality evaluation unit calculates an evaluation value indicating an evaluation of an image quality of an ultrasound image. The notification unit notifies a user of an image quality parameter for adjusting the image quality of the ultrasound image. In a case where the evaluation value is equal to or less than a predetermined threshold value, the notification unit notifies the user of the image quality parameter for increasing the evaluation value.

13 Claims, 7 Drawing Sheets

ULTRASOUND DIAGNOSTIC APPARATUS AND PROGRAM

CROSS-REFERENCE TO RELATED APPLICATIONS

This application claims benefit of priority to Japanese Patent Application No. 2024-014475 filed Feb. 1, 2024, the entire contents of which are incorporated herein by reference.

BACKGROUND OF THE INVENTION

1. Field of the Invention

The present disclosure relates to an ultrasound diagnostic apparatus and a program.

2. Description of the Related Art

In order to generate an ultrasound image suitable for an ultrasound examination, an image quality parameter for adjusting an image quality of the ultrasound image may be changed.

JP2010-274111A discloses a system that automatically adjusts parameters according to an ultrasound image in order to clarify the ultrasound image.

JP1993-253220A (JP-H5-253220A) discloses an ultrasound diagnostic apparatus in which a user can change a preset value of a parameter.

SUMMARY OF THE INVENTION

In general, it is difficult for a user to manually change an image quality parameter such that an ultrasound image having a desired image quality is generated. In addition, it takes time to adjust the image quality.

An object of the present disclosure is to support a user in changing an image quality parameter for adjusting an image quality of an ultrasound image.

According to an aspect of the present disclosure, there is provided an ultrasound diagnostic apparatus comprising: a calculation unit that calculates, based on a reception signal acquired by transmission and reception of ultrasound waves, an evaluation value indicating an evaluation of an image quality of an ultrasound image generated based on the reception signal; and a notification unit that notifies a user of an image quality parameter for adjusting the image quality of the ultrasound image, in which in a case where the evaluation value is equal to or less than a predetermined threshold value, the notification unit notifies the user of the image quality parameter for increasing the evaluation value.

The notification unit may notify the user of a change direction of the image quality parameter for increasing the evaluation value.

An evaluation item for evaluating the image quality of the ultrasound image may be determined for each diagnostic site where the ultrasound waves are transmitted and received, the threshold value may be predetermined for each diagnostic site, the calculation unit may calculate an evaluation value for the evaluation item for evaluating the image quality of the ultrasound image of the diagnostic site where the ultrasound waves are transmitted and received, based on the reception signal, and in a case where the evaluation value is equal to or less than the threshold value for the diagnostic site, the notification unit may notify the user of the change direction of the image quality parameter for increasing the evaluation value.

A plurality of evaluation items for evaluating the image quality of the ultrasound image may be predetermined, the calculation unit may calculate, for each evaluation item, an individual evaluation value for the evaluation item based on the reception signal, and the notification unit may further notify the user of each calculated individual evaluation value.

The calculation unit may further calculate an evaluation value, which is calculated in a case where the image quality parameter is changed according to the change direction, as an estimated evaluation value, and the notification unit may further notify the user of the estimated evaluation value.

The calculation unit may calculate the evaluation value based on the reception signal included in a region of interest.

A plurality of evaluation items for evaluating the image quality of the ultrasound image may be predetermined, the calculation unit may calculate an individual evaluation value for an evaluation item selected by the user from among the plurality of evaluation items, and the notification unit may further notify the user of the calculated individual evaluation value.

The notification unit may further display an ultrasound image generated based on a changed image quality parameter for increasing the individual evaluation value for each evaluation item, on a display.

The calculation unit may further calculate a recommended value of the image quality parameter for increasing the evaluation value, and the notification unit may further notify the user of the recommended value.

According to another aspect of the present disclosure, there is provided a program for causing a computer to function as: a calculation unit that calculates, based on a reception signal acquired by transmission and reception of ultrasound waves, an evaluation value indicating an evaluation of an image quality of an ultrasound image generated based on the reception signal; and a notification unit that notifies a user of an image quality parameter for adjusting the image quality of the ultrasound image, in which in a case where the evaluation value is equal to or less than a predetermined threshold value, the notification unit notifies the user of the image quality parameter for increasing the evaluation value.

According to the present disclosure, it is possible to support the user in changing the image quality parameter for adjusting the image quality of the ultrasound image.

DESCRIPTION OF THE PREFERRED EMBODIMENTS

First Embodiment

Figure 1:
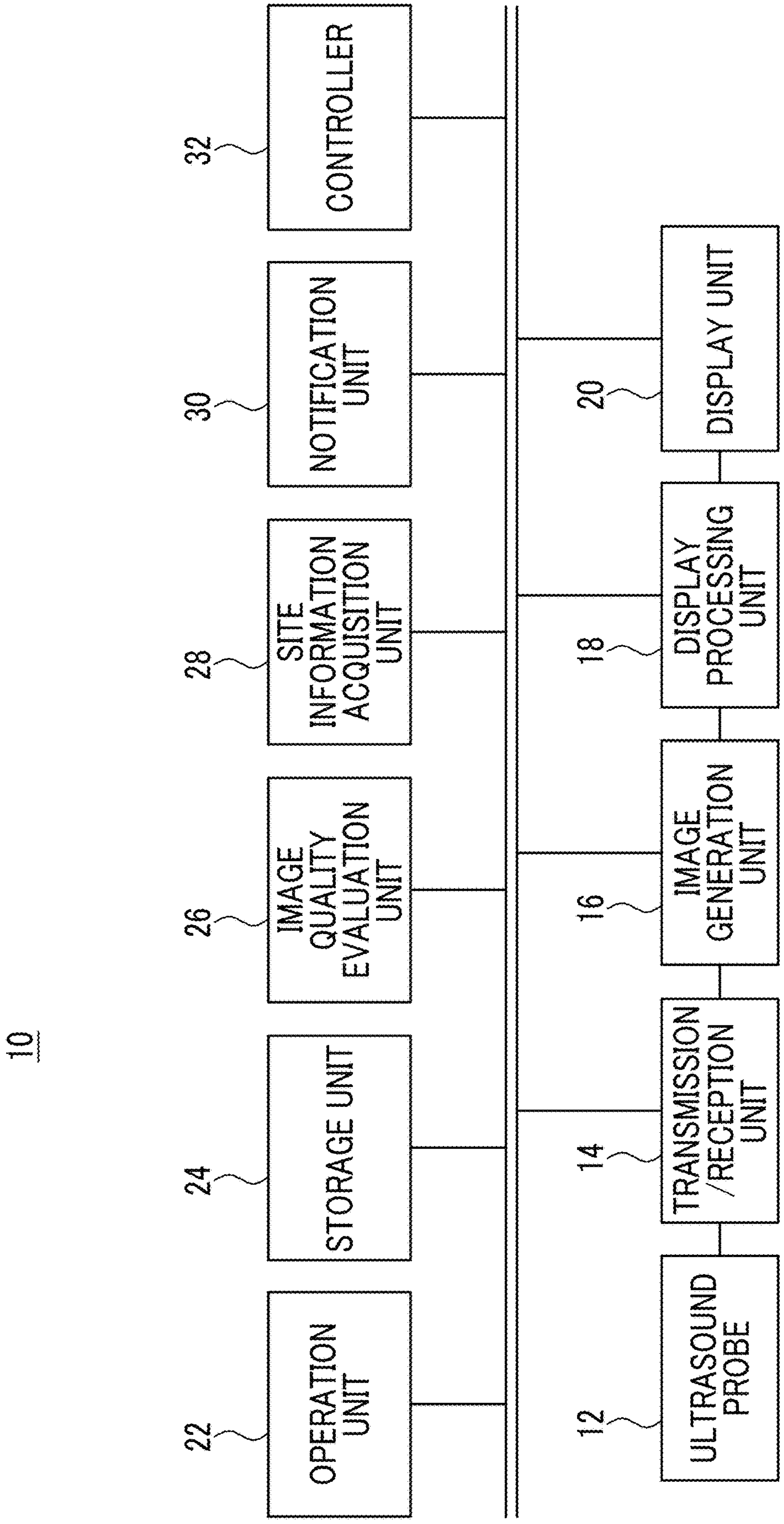
FIG. 1 is a block diagram showing a configuration of an ultrasound diagnostic apparatus according to a first embodiment.

An ultrasound diagnostic apparatus 10 according to a first embodiment will be described with reference to FIG. 1. FIG. 1 is a block diagram showing an example of a configuration of the ultrasound diagnostic apparatus 10 according to the first embodiment.

The ultrasound diagnostic apparatus 10 generates ultrasound image data by transmitting and receiving ultrasound waves using an ultrasound probe 12. For example, the ultrasound diagnostic apparatus 10 transmits the ultrasound waves into a subject and receives the ultrasound waves reflected from the inside of the subject to generate the ultrasound image data representing a tissue inside the subject.

The ultrasound probe 12 is a device that transmits and receives the ultrasound waves. The ultrasound probe 12 includes, for example, a 1D array oscillator. The 1D array oscillator includes a plurality of ultrasound oscillators arranged one-dimensionally. An ultrasound beam is formed by the 1D array oscillator, and electronic scanning with the ultrasound beam is repeatedly performed. As a result, a scanning cross section is formed in a living body for each electronic scanning. The scanning cross section corresponds to a two-dimensional echo data acquisition space. The ultrasound probe 12 may include a 2D array oscillator in which a plurality of ultrasound oscillators are formed two-dimensionally. In a case where the ultrasound beam is formed by the 2D array oscillator, and the electronic scanning with the ultrasound beam is repeatedly performed, the scanning cross section as the two-dimensional echo data acquisition space is formed for each electronic scanning. In a case where the scanning with the ultrasound beam is performed two-dimensionally, a three-dimensional space as a three-dimensional echo data acquisition space is formed. As a scanning method, sector scanning, linear scanning, convex scanning, or the like is used.

A transmission/reception unit 14 functions as a transmission beam former and a reception beam former. In the transmission, the transmission/reception unit 14 supplies a plurality of transmission signals having a certain delay relationship with the plurality of ultrasound oscillators included in the ultrasound probe 12. As a result, a transmission beam of the ultrasound waves is formed. In the reception, reflected waves from the living body are received by the ultrasound probe 12, whereby a plurality of reception signals (RF signals) are output from the ultrasound probe 12 to the transmission/reception unit 14. The transmission/reception unit 14 forms a reception beam by applying phasing addition processing to the plurality of reception signals. Data of the reception beam is output to an image generation unit 16. That is, the transmission/reception unit 14 forms the reception beam by performing delay processing on the reception signal obtained from each ultrasound oscillator according to a delay processing condition for each ultrasound oscillator and performing addition processing on the plurality of reception signals obtained from the plurality of ultrasound oscillators. The delay processing condition is defined by reception delay data indicating a delay time. A reception delay data set (that is, a set of delay times) corresponding to the plurality of ultrasound oscillators is supplied from a controller 32.

The electronic scanning with the ultrasound beam (that is, the transmission beam and the reception beam) is performed by the action of the transmission/reception unit 14, thereby forming the scanning cross section. The scanning cross section corresponds to a plurality of beams, and the plurality of beams constitute a reception frame (specifically, an RF signal frame). Each beam is configured by a plurality of echoes arranged in a depth direction. By repeating the electronic scanning with the ultrasound beam, a plurality of reception frames arranged on a time axis are output from the transmission/reception unit 14 to the image generation unit 16. The plurality of reception frames constitute a reception frame sequence.

In a case where the electronic scanning with the ultrasound beam is performed two-dimensionally by the action of the transmission/reception unit 14, the three-dimensional echo data acquisition space is formed, and volume data as an echo data aggregate is acquired from the three-dimensional echo data acquisition space. By repeating the electronic scanning with the ultrasound beam, a plurality of volume data arranged on a time axis are output from the transmission/reception unit 14 to the image generation unit 16. The plurality of volume data constitute a volume data sequence.

The image generation unit 16 generates ultrasound image data (for example, B-mode image data) by applying signal processing such as detection, amplitude compression (for example, logarithmic compression), and a conversion function (a coordinate conversion function and an interpolation processing function by a digital scan converter (DSC)) to the reception frame output from the transmission/reception unit 14.

Hereinafter, the image data will be referred to as an "image" as appropriate. For example, the ultrasound image data is referred to as an "ultrasound image" as appropriate, and the B-mode image data is referred to as a "B-mode image" as appropriate. The ultrasound image is not limited to the B-mode image and may be any image generated by the transmission and reception of the ultrasound waves. For example, the ultrasound image may be a color Doppler image, a pulse Doppler image, a strain image, a shear wave elastography image, or the like.

A display processing unit 18 generates a display image by overlaying necessary graphic data on the ultrasound image. The display image is output to a display unit 20. One or a plurality of images are arranged and displayed in a display aspect according to a display mode.

The display unit 20 is a display such as a liquid crystal display or an EL display. The ultrasound image such as the B-mode image is displayed on the display unit 20. The display unit 20 may be a device comprising both the display and an operation unit 22. For example, a graphic user interface (GUI) may be realized by the display unit 20 and the operation unit 22. In addition, a user interface such as a touch panel may be realized by the display unit 20 and the operation unit 22.

The operation unit 22 is a device for the user to input an imaging condition, a command, or the like to the ultrasound diagnostic apparatus 10. For example, the operation unit 22 is an operation panel, a switch, a button, a keyboard, a mouse, a track ball, or a joystick.

A storage unit 24 constitutes one or a plurality of storage regions for storing data. For example, the storage unit 24 is a hard disk drive (HDD), a solid state drive (SSD), various memories (for example, RAM, DRAM, or ROM), other storage devices (for example, optical disk), or a combination thereof.

For example, the reception signal, the reception beam generated based on the reception signal, the reception frame, the volume data, the ultrasound image, information indicating the imaging condition, information related to the subject (for example, the patient), and the like are stored in the storage unit 24.

Based on a reception signal acquired by the transmission and reception of the ultrasound waves, an image quality evaluation unit 26 calculates an evaluation value indicating an evaluation of the image quality of the ultrasound image generated based on the reception signal. The image quality evaluation unit 26 may calculate an evaluation value indicating the evaluation of the image quality of the ultrasound image based on the reception frame or the ultrasound image. That is, the image quality evaluation unit 26 may calculate the evaluation value based on the reception signal, may calculate the evaluation value based on the reception frame output from the transmission/reception unit 14, or may calculate the evaluation value based on the ultrasound image output from the image generation unit 16. In the following, for convenience of description, processing of calculating the evaluation value based on the reception signal will be described. However, the image quality evaluation unit 26 may calculate the evaluation value based on the reception frame or the ultrasound image. The image quality evaluation unit 26 corresponds to an example of a calculation unit.

One or a plurality of evaluation items for evaluating the image quality of the ultrasound image are predetermined. For example, the evaluation items include a contrast, a spatial resolution, a signal noise ratio (SNR) of an image, and the like. Of course, the evaluation items other than these may be used. The evaluation item can be said to be a viewpoint for evaluating the image quality of the ultrasound image (that is, an evaluation viewpoint).

The image quality evaluation unit 26 calculates an evaluation value of the ultrasound image based on the reception signal for each evaluation item. Hereinafter, the evaluation value for each evaluation item will be referred to as an "individual evaluation value". That is, the image quality evaluation unit 26 calculates, for each evaluation item, the individual evaluation value for the evaluation item.

In addition, the image quality evaluation unit 26 calculates a comprehensive evaluation value (hereinafter, referred to as an "overall evaluation value") based on one or a plurality of individual evaluation values. A weighted average or the like may be used in order to calculate the overall evaluation value. In a case where only one evaluation item is used, the individual evaluation value for the evaluation item is the overall evaluation value. In a case where a plurality of evaluation items are used, the image quality evaluation unit 26 calculates the overall evaluation value based on a plurality of individual evaluation values.

A method of calculating the individual evaluation value and the overall evaluation value will be described in detail later.

In addition, in a case where the calculated evaluation value is equal to or less than a predetermined threshold value, the image quality evaluation unit 26 specifies one or a plurality of image quality parameters for increasing the evaluation value. For example, one or a plurality of evaluation items and one or a plurality of image quality parameters are associated in advance, and information indicating the association is stored in the storage unit 24 in advance. It is calculated in advance or learned by machine learning or the like how the individual evaluation value of each of one or a plurality of evaluation items associated with a certain image quality parameter is changed depending on how the image quality parameter is changed. Therefore, in a case where it is desired to increase the evaluation value, it is possible to specify the image quality parameter to be changed. In addition, it is possible to know what value should be set for the image quality parameter to be changed in order to obtain a target evaluation value. That is, it is possible to specify a change direction of the image quality parameter (that is, a correction direction of the image quality parameter) for obtaining the target evaluation value. The image quality evaluation unit 26 specifies the change direction of the image quality parameter to be changed.

For example, the image quality parameter is a transmission frequency, the number of frames to be smoothed, a gain, a transmission focus, a scan line density, a dynamic range, a brightness gamma curve, the number of compounds, and the like.

For example, in a case where an individual evaluation value of a certain evaluation item is equal to or less than a threshold value, the image quality evaluation unit 26 specifies one or a plurality of image quality parameters for increasing the individual evaluation value (that is, one or a plurality of image quality parameters associated with the evaluation item) based on the information indicating the association. In addition, the image quality evaluation unit 26 specifies a change direction of the specified one or plurality of image quality parameters based on the information indicating the association.

In a case where the overall evaluation value is equal to or less than a threshold value, the image quality evaluation unit 26 may specify one or a plurality of image quality parameters for increasing the overall evaluation value, and may further specify a change direction of the specified one or plurality of image quality parameters.

The image quality evaluation unit 26 outputs the individual evaluation value, the overall evaluation value, the information indicating one or a plurality of image quality parameters for increasing the evaluation value, and the information indicating the change direction of the image quality parameter to a notification unit 30.

A site information acquisition unit 28 acquires information indicating a diagnostic site where the ultrasound waves are transmitted and received (hereinafter, referred to as "diagnostic site information").

For example, in a case where the user designates the diagnostic site by operating the operation unit 22 at a start of an ultrasound examination, the site information acquisition unit 28 acquires the diagnostic site information indicating the diagnostic site designated by the user. In a case where the diagnostic site is preset, the site information acquisition unit 28 may acquire the diagnostic site information from preset information set at the start of the examination.

As another example, the site information acquisition unit 28 may apply site recognition processing to the ultrasound image generated by the transmission and reception of the ultrasound waves to recognize the diagnostic site from the ultrasound image, thereby acquiring the diagnostic site information.

As the site recognition processing, known site recognition processing is used. For example, machine learning or artificial intelligence (AI) may be used for the site recognition processing. A type of the artificial intelligence or machine learning to be used is not limited, and any algorithm or model may be used. For example, a convolutional neural network (CNN), a recurrent neural network (RNN), generative adversarial networks (GAN), linear models, random forests, decision tree learning, a support vector machine (SVM), an ensemble classifier, or other algorithms are used. In addition, pattern matching such as template matching, or an algorithm that does not require learning, such as a correlation coefficient or similarity calculation, may be used for the site recognition processing.

Pattern matching using a standard cross-sectional image (for example, a B-mode image) may be used as the site recognition processing. For example, one or a plurality of standard cross-sectional images are generated in advance for each diagnostic site and are stored in the storage unit 24 or an external device. The site information acquisition unit 28 specifies the diagnostic site where the ultrasound waves are transmitted and received by comparing the ultrasound image generated by the transmission and reception of the ultrasound waves with each standard cross-sectional image, thereby acquiring the diagnostic site information.

The site information acquisition unit 28 outputs the diagnostic site information to the image quality evaluation unit 26 and the notification unit 30. As will be described below, the image quality evaluation unit 26 may calculate an individual evaluation value for an evaluation item corresponding to the diagnostic site indicated by the diagnostic site information.

The notification unit 30 notifies the user of various types of information. For example, the notification unit 30 may display various types of information on the display unit 20 or may output various types of information as audio information from a speaker.

For example, the notification unit 30 notifies the user of the information output from the image quality evaluation unit 26 or the diagnostic site information output from the site information acquisition unit 28. Specifically, the notification unit 30 notifies the user of at least one of the individual evaluation value, the overall evaluation value, the information indicating one or a plurality of the image quality parameters for increasing the evaluation value, or the information indicating the change direction of the image quality parameter.

The controller 32 controls each unit of the ultrasound diagnostic apparatus 10.

Hereinafter, an example of processing by the image quality evaluation unit 26 will be described.

Individual evaluation values x1, x2, . . . , xN are defined. For example, a contrast, a spatial resolution, and an SNR of the ultrasound image are set as evaluation items (that is, evaluation viewpoints). An individual evaluation value for the contrast is defined as the individual evaluation value x1. An individual evaluation value for the spatial resolution is defined as the individual evaluation value x2. An individual evaluation value for the SNR is defined as the individual evaluation value x3.

For example, a spread value of a brightness distribution obtained from a standard deviation value of the brightness distribution in the ultrasound image or the like is used to calculate the individual evaluation value x1 for the contrast of the ultrasound image. In general, as the spread of the brightness distribution is larger, the contrast of the image is higher. The image quality evaluation unit 26 calculates, as the individual evaluation value x1 for the contrast, a ratio (%) of a spread value of a brightness distribution calculated from the reception signal or the ultrasound image input to the image quality evaluation unit 26 with respect to a spread value of a standard brightness distribution determined in advance. The spread value of the standard brightness distribution is stored in the storage unit 24 or an external device in advance.

For example, as the spatial resolution, a spread value of a frequency spectrum distribution of the reception signal in a region where the brightness distribution of the ultrasound image is flat is used. In general, as the frequency spectrum is wider, signal characteristics are higher, and an image with a higher spatial resolution is generated. The image quality evaluation unit 26 calculates, as the individual evaluation value x2 for the spatial resolution, a ratio (%) of a spread value of a frequency spectrum distribution calculated from the reception signal or the ultrasound image input to the image quality evaluation unit 26 with respect to a spread value of a standard frequency spectrum distribution determined in advance. The spread value of the standard frequency spectrum distribution is stored in the storage unit 24 or an external device in advance.

For example, an average brightness value of the ultrasound image is used as the SNR. In general, since noise is generated from a system including the ultrasound diagnostic apparatus 10, a level of the noise is constant or almost constant. On the other hand, a brightness of the ultrasound image changes depending on the subject. In addition, as a brightness level of the ultrasound image is higher, the SNR is higher. The image quality evaluation unit 26 calculates, as the individual evaluation value x3 for the SNR, a ratio (%) of an average brightness value calculated from the reception signal or the ultrasound image input to the image quality evaluation unit 26 with respect to a standard average brightness value determined in advance. The standard average brightness value is stored in advance in the storage unit 24 or an external device.

The image quality evaluation unit 26 calculates an overall evaluation value S according to the following Equation (1). That is, the image quality evaluation unit 26 calculates an average value of the individual evaluation values x1, x2, . . . , xN as the overall evaluation value S.

Equation 1

$$S = \frac{1}{N}\sum_{k} x_k \tag{1}$$

As another example, the image quality evaluation unit 26 may calculate the overall evaluation value S according to the following Equation (2). That is, the image quality evaluation unit 26 may calculate a weighted average value of the individual evaluation values x1, x2, . . . , xN as the overall evaluation value S.

Equation 2

$$S = \frac{1}{N}\sum_{k} w_k x_k \tag{2}$$

Here, a coefficient $w_k$ may be designated by the user or may be determined for each diagnostic site.

The image quality evaluation unit 26 decides the change direction of the image quality parameter and a priority of the image quality parameter to be changed according to each individual evaluation value $x_k$ and the overall evaluation value S.

As described above, one or a plurality of evaluation items and one or a plurality of image quality parameters are associated in advance, and information indicating the association is stored in the storage unit 24 in advance. For example, the image quality evaluation unit 26 specifies the individual evaluation value $x_k$ lower than the overall evaluation value S, and specifies one or a plurality of image quality parameters related to the specified individual evaluation value $x_k$ (that is, one or a plurality of image quality parameters associated with the individual evaluation value $x_k$). In addition, the image quality evaluation unit 26 specifies a change direction of the specified one or plurality of image quality parameters (that is, a direction in which the image quality parameter is to be increased or decreased). The notification unit 30 displays the specified one or plurality of image quality parameters and information indicating the change direction of each image quality parameter on the display unit 20.

In a case where a plurality of individual evaluation values $x_k$ are lower than the overall evaluation value S, the image quality evaluation unit 26 specifies one or a plurality of image quality parameters related to each of the plurality of individual evaluation values $x_k$ (that is, one or a plurality of image quality parameters associated with each of the plurality of individual evaluation values $x_k$). In addition, the image quality evaluation unit 26 specifies a change direction of the specified one or plurality of image quality parameters. The notification unit 30 displays the specified one or plurality of image quality parameters and information indicating the change direction of each image quality parameter on the display unit 20.

In addition, the image quality evaluation unit 26 may determine the priority of the image quality parameter to be changed in ascending order of the individual evaluation value with respect to the overall evaluation value S. For example, the image quality evaluation unit 26 assigns a higher priority to the image quality parameter associated with a lower individual evaluation value. The notification unit 30 may display information indicating the priority together with the image quality parameter to be changed on the display unit 20.

For example, the image quality parameter related to the evaluation item "contrast" is a gain, the number of frames to be smoothed (noise reduction), and the like. That is, the gain, the number of frames to be smoothed, and the like are associated in advance with the evaluation item "contrast", and information indicating the association is stored in the storage unit 24 in advance. In addition, how the evaluation item "contrast" is changed depending on how the gain is changed is calculated in advance or learned by machine learning or the like, and information indicating contents thereof is stored in the storage unit 24 in advance. Similarly, how the evaluation item "contrast" is changed depending on how the number of frames to be smoothed is changed is calculated in advance or learned by machine learning or the like, and information indicating contents thereof is stored in the storage unit 24 in advance.

The image quality parameter related to the evaluation item "spatial resolution" is the transmission frequency, the scan line density, and the like. That is, the transmission frequency, the scan line density, and the like are associated in advance with the evaluation item "spatial resolution", and information indicating the association is stored in the storage unit 24 in advance. In addition, how the evaluation item "spatial resolution" is changed depending on how the transmission frequency is changed is calculated in advance or learned by machine learning or the like, and information indicating contents thereof is stored in the storage unit 24 in advance. The same applies to the scan line density.

The image quality parameter related to the evaluation item "SNR" is the transmission frequency, the number of frames to be smoothed, and the like. That is, the transmission frequency, the number of frames to be smoothed, and the like are associated in advance with the evaluation item "SNR", and information indicating the association is stored in the storage unit 24 in advance. In addition, how the evaluation item "SNR" is changed depending on how the transmission frequency is changed is calculated in advance or learned by machine learning or the like, and information indicating contents thereof is stored in the storage unit 24 in advance. The same applies to the number of frames to be smoothed.

For example, in a case where the individual evaluation value x1 for the evaluation item "contrast" is lower than the overall evaluation value S, the image quality evaluation unit 26 specifies the image quality parameters "gain", "the number of frames to be smoothed", and the like associated with the evaluation item "contrast" as the image quality parameter to be changed. In addition, the image quality evaluation unit 26 specifies a change direction of the specified image quality parameter. The notification unit 30 displays information indicating the image quality parameter "gain" and information indicating a change direction of the image quality parameter "gain" on the display unit 20. The same applies to the number of frames to be smoothed and the like.

Hereinafter, each example of the first embodiment will be described.

Example 1-1

Figure 2:
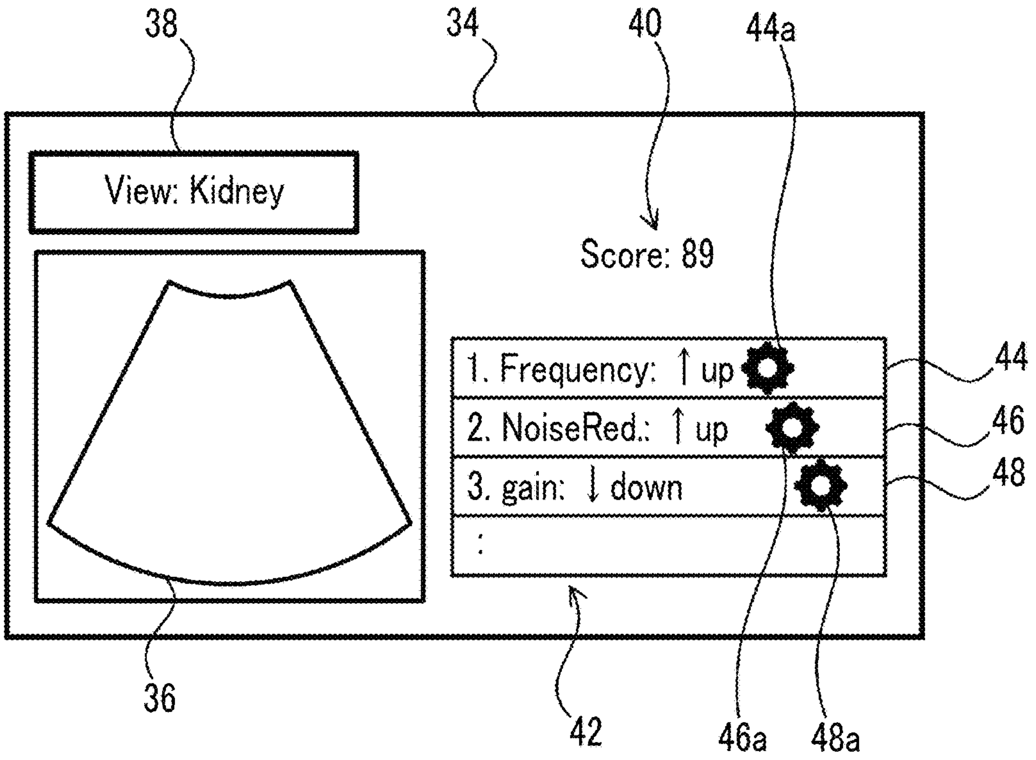
FIG. 2 is a diagram showing a screen displaying an evaluation value and an image quality parameter.

Example 1-1 will be described with reference to FIGS. 1 and 2. FIG. 2 shows a screen displaying an evaluation value and an image quality parameter.

A screen 34 is displayed on the display unit 20. In a case where an ultrasound image 36 is generated by the image generation unit 16, an ultrasound image 36 is displayed on the screen 34. Here, as an example, the ultrasound image 36 is a B-mode image. Of course, a Doppler image or the like may be displayed as the ultrasound image 36.

In a case where the site information acquisition unit 28 acquires the diagnostic site information, the notification unit 30 displays the diagnostic site information on the screen 34 as indicated by a reference numeral 38. Here, as an example, "Kidney" is the diagnostic site.

The notification unit 30 displays the evaluation value ("Score" in FIG. 2) on the screen 34 as indicated by a reference numeral 40. For example, the notification unit 30 displays the overall evaluation value S on the screen 34. In the example shown in FIG. 2, the overall evaluation value S is "89".

In a case where the overall evaluation value S is equal to or less than a threshold value, the notification unit 30 displays the image quality parameter for increasing the overall evaluation value S (that is, the image quality parameter to be changed) on the screen 34. In the example shown in FIG. 2, since the overall evaluation value S is equal to or less than the threshold value, the notification unit 30 displays the image quality parameter to be changed on the screen 34.

For example, the notification unit 30 displays a list 42 of the image quality parameters to be changed on the screen 34. As described above, the image quality parameter to be changed is specified by the image quality evaluation unit 26. Here, as an example, "transmission frequency" ("Frequency" in FIG. 2) indicated by a reference numeral 44, "the number of frames to be smoothed" ("NoiseRed" in FIG. 2) indicated by a reference numeral 46, and "gain" indicated by a reference numeral 48 are specified as the image quality parameters to be changed. The notification unit 30 displays these image quality parameters on the screen 34.

In the example shown in FIG. 2, the notification unit 30 displays each image quality parameter on the screen 34 according to the priority. For example, the image quality parameter "transmission frequency" is ranked first (that is, the highest priority). The image quality parameter "the number of frames to be smoothed" is ranked second. The image quality parameter "gain" is ranked third.

In addition, a change direction of each image quality parameter to be changed is specified by the image quality evaluation unit 26. The notification unit 30 displays information indicating the change direction of each image quality parameter to be changed on the screen 34. For example, the notification unit 30 represents the change direction by a character string "up", a character string "down", a symbol "upward arrow", and a symbol "downward arrow".

For example, a change direction of the image quality parameter "transmission frequency" is specified as a direction in which the image quality parameter is increased (that is, a direction in which the frequency is increased). That is, the overall evaluation value S can be increased by increasing the image quality parameter "transmission frequency". In this case, the notification unit 30 displays a character string "up" and a symbol "upward arrow" on the screen 34 as information indicating the change direction of the image quality parameter "transmission frequency".

In addition, the change direction of the image quality parameter "gain" is specified as a direction in which the image quality parameter is decreased (that is, a direction in which the gain is decreased). That is, the overall evaluation value S can be increased by decreasing the image quality parameter "gain". In this case, the notification unit 30 displays a character string "down" and a symbol "downward arrow" on the screen 34 as information indicating the change direction of the image quality parameter "gain".

The notification unit 30 displays the information indicating the change direction on the screen 34 for other image quality parameters in the same manner.

In addition, the notification unit 30 displays change buttons 44*a*, 46*a*, and 48*a* on the screen 34. The change button 44*a* is a button for changing the image quality parameter "transmission frequency". The change button 46*a* is a button for changing the image quality parameter "the number of frames to be smoothed". The change button 48*a* is a button for changing the image quality parameter "gain". By operating a change button, the user can change the image quality parameter corresponding to that change button.

As described above, each image quality parameter to be changed and the information indicating the change direction of each image quality parameter are displayed on the screen 34 and presented to the user. In this manner, the user can easily understand each image quality parameter to be changed and the change direction of each image quality parameter. As a result, according to Example 1-1, it is possible to support the user in changing the image quality parameter for adjusting the image quality of the ultrasound image.

Example 1-2

In Example 1-2, one or a plurality of evaluation items suitable for evaluating the image quality of the ultrasound image indicating the diagnostic site are predetermined for each diagnostic site. For example, diagnostic site information indicating a diagnostic site and information indicating one or a plurality of evaluation items suitable for evaluating an image quality of an ultrasound image indicating the diagnostic site are associated in advance and stored in advance in the storage unit 24.

For example, in a case where the diagnostic site is a mammary gland, a spatial resolution in a depth direction and a contrast are evaluation items suitable for the evaluation of the image quality. Therefore, the diagnostic site information indicating the diagnostic site "mammary gland" and the information indicating the evaluation item "spatial resolution in a depth direction" and the evaluation item "contrast" are associated in advance and stored in advance in the storage unit 24.

In a case where the diagnostic site is a liver, penetration and speckle reduction are evaluation items suitable for the evaluation of the image quality. Therefore, the diagnostic site information indicating the diagnostic site "liver" and the information indicating the evaluation items "penetration" and "speckle reduction" are associated in advance and stored in advance in the storage unit 24.

The site information acquisition unit 28 acquires diagnostic site information indicating a diagnostic site where the ultrasound waves are transmitted and received. The image quality evaluation unit 26 calculates an individual evaluation value for an evaluation item for evaluating the image quality of the ultrasound image of the diagnostic site indicated by the diagnostic site information. That is, the image quality evaluation unit 26 calculates an individual evaluation value of each of one or a plurality of evaluation items associated with the diagnostic site. For example, in a case where the diagnostic site is "mammary gland", the image quality evaluation unit 26 calculates an individual evaluation value for the evaluation item "spatial resolution in a depth direction" and an individual evaluation value for the evaluation item "contrast". In addition, the image quality evaluation unit 26 calculates the overall evaluation value S based on these individual evaluation values.

For example, in a case where the overall evaluation value S is equal to or less than the threshold value, as shown in FIG. 2, the notification unit 30 displays the image quality parameter for increasing the overall evaluation value S (that is, the image quality parameter to be changed) on the screen 34. The image quality parameter to be changed is specified in the same manner as in Example 1-1.

In Example 1-2, the above-described threshold value is predetermined for each diagnostic site. For example, a threshold value for the diagnostic site "mammary gland" and a threshold value for the diagnostic site "liver" are predetermined and stored in advance in the storage unit 24. In a case where the diagnostic site is "mammary gland and the overall evaluation value S is equal to or less than the threshold value for the mammary gland, the notification unit 30 displays the image quality parameter for increasing the overall evaluation value S on the screen 34. The same applies to other diagnostic sites.

In Example 1-2, in order to calculate the individual evaluation value x1 described above, a spread value of a standard brightness distribution determined according to the diagnostic site is used as a spread value of a standard brightness distribution determined in advance. Similarly, in order to calculate the individual evaluation value x2 described above, a spread value of a standard frequency spectrum distribution determined according to the diagnostic site is used as a spread value of a standard frequency spectrum distribution determined in advance. In order to calculate the individual evaluation value x3 described above, a standard average brightness value determined according to the diagnostic site is used with a standard average brightness value determined in advance as a reference.

According to Example 1-2, by evaluating the image quality according to the evaluation item suitable for evaluating the image quality of the ultrasound image indicating the diagnostic site, it is possible to support the user in changing the image quality parameter for adjusting the image quality of the ultrasound image indicating the diagnostic site.

In Example 1-2, in a case where the diagnostic site designated by the user and the diagnostic site recognized by the site recognition processing are different from each other, the notification unit 30 may display information prompting correction of the diagnostic site designated by the user on the display unit 20. For example, the user inputs the diagnostic site information indicating the diagnostic site to the ultrasound diagnostic apparatus 10 by using the operation unit 22. In addition, the site information acquisition unit 28 applies the site recognition processing to the ultrasound image to recognize the diagnostic site. In a case where the diagnostic site designated by the user and the diagnostic site recognized by the site recognition processing are different from each other, the notification unit 30 displays information prompting correction of the diagnostic site on the display unit 20. For example, the notification unit 30 displays a message indicating that the diagnostic site designated by the user and an automatically recognized diagnostic site are different from each other on the display unit 20. In a case where the user corrects the diagnostic site using the operation unit 22, the processing according to Example 1-2 is executed for the corrected diagnostic site.

In addition, in a case where the diagnostic site recognized by the diagnostic site recognition processing is different from an actual diagnostic site, the notification unit 30 may display information for correcting the diagnostic site on the display unit 20. For example, in a case where the user corrects the diagnostic site using the operation unit 22, the processing according to Example 1-2 is executed for the corrected diagnostic site.

Example 1-3

In Example 1-3, the image quality evaluation unit 26 may calculate the individual evaluation value and the overall evaluation value in real time during the transmission and reception of the ultrasound waves, may calculate the individual evaluation value and the overall evaluation value after the ultrasound images of a predetermined number of frames are acquired, or may calculate the individual evaluation value and the overall evaluation value after a predetermined time has elapsed from a certain point in time (for example, an imaging start point in time).

For example, by calculating the individual evaluation value and the overall evaluation value in real time, even in a case where a location (for example, a cross section) where the ultrasound waves are transmitted and received is changed, the image quality can be evaluated following the change. As a result, the user can easily associate the operation of the ultrasound probe 12 with the evaluation value, and can quickly decide how to operate the ultrasound probe 12 (for example, how to press the ultrasound probe 12).

Example 1-4

In Example 1-4, in a case where there is an instruction from the user, the image quality evaluation unit 26 calculates the individual evaluation value and the overall evaluation value.

The user can give an instruction to the image quality evaluation unit 26 by operating the operation unit 22. An image (for example, an icon or a button image) forgiving the instruction may be displayed on the display unit 20, and the user may give the instruction to the image quality evaluation unit 26 by, for example, pressing the image.

For example, the image quality evaluation unit 26 may calculate the individual evaluation value and the overall evaluation value in real time until the user gives an instruction to stop the evaluation, or may calculate the individual evaluation value and the overall evaluation value in a case where the user gives an instruction to perform the evaluation.

According to Example 1-4, since the image quality is evaluated at a timing desired by the user, unnecessary notification is not given to the user.

Example 1-5

Figure 3:
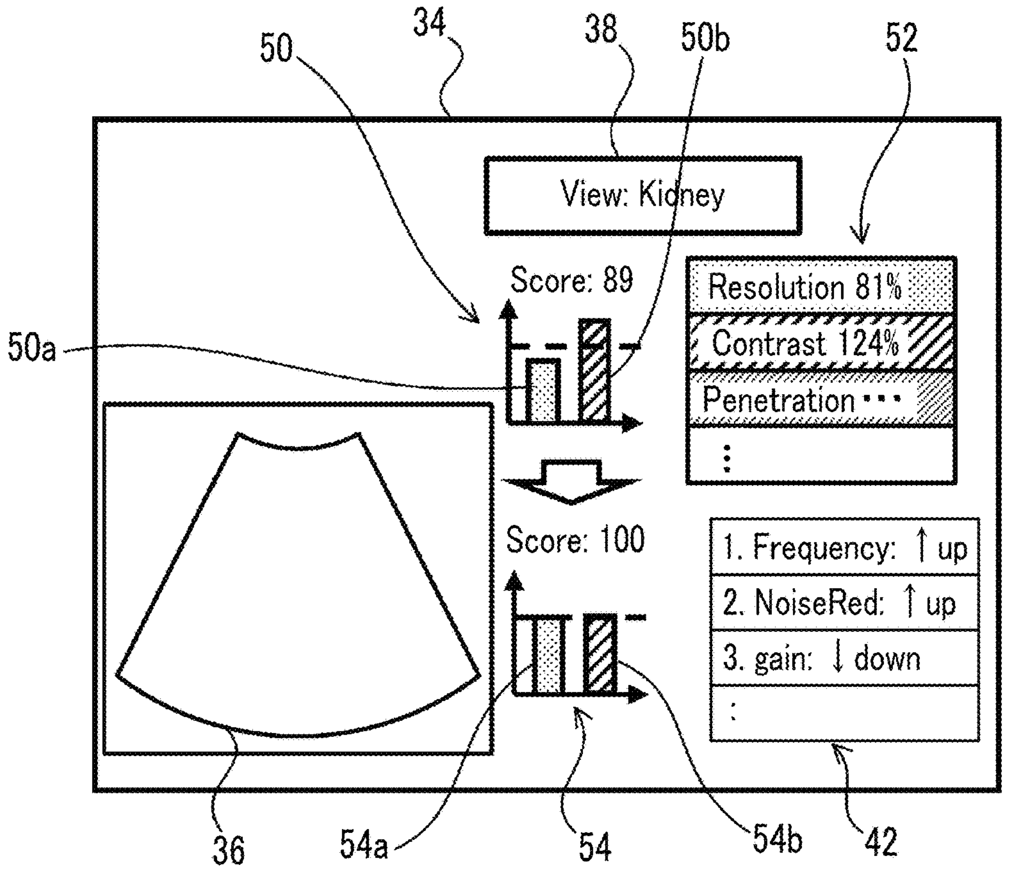
FIG. 3 is a diagram showing a screen displaying an evaluation value and an image quality parameter.

Example 1-5 will be described with reference to FIG. 3. FIG. 3 shows a screen displaying an evaluation value and an image quality parameter.

In Example 1-5, the notification unit 30 displays the individual evaluation value of each evaluation item on the display unit 20. The notification unit 30 may display the overall evaluation value on the display unit 20 and display the individual evaluation value of each evaluation item on the display unit 20, or may display the individual evaluation value of each evaluation item on the display unit 20 without displaying the overall evaluation value on the display unit 20.

A screen 34 shown in FIG. 3 is displayed on the display unit 20. As in the example shown in FIG. 2, the ultrasound image 36, the information indicating the diagnostic site (reference numeral 38), and the list 42 of the image quality parameters to be changed are displayed on the screen 34. In the list 42, the information indicating the change direction of each image quality parameter is shown.

In addition, in Example 1-5, the notification unit 30 displays a graph 50 representing each individual evaluation value and a list 52 of the individual evaluation values on the screen 34. In addition, the notification unit 30 displays a score as the overall evaluation value on the screen 34. “Score: 89” in FIG. 3 is an overall evaluation value before the image quality parameter is changed.

For example, an individual evaluation value for each of evaluation items such as “Resolution”, “Contrast”, and “Penetration” is calculated, and these individual evaluation values are included in the list 52. As in Example 1-2, an individual evaluation value for each individual evaluation associated with the diagnostic site may be calculated.

For example, the individual evaluation value of the evaluation item “Resolution” is 81%. The individual evaluation value of the evaluation item “Contrast” is 124%. A graph 50*a* represents the individual evaluation value of the evaluation item “Resolution”. A graph 50*b* represents the individual evaluation value of the evaluation item “Contrast”. As described above, the individual evaluation values for the evaluation items are visualized by the graphs.

In Example 1-5, the image quality evaluation unit 26 calculates an evaluation value, which is calculated in a case where the image quality parameter is changed according to the change direction, as an estimated evaluation value. The notification unit 30 displays the estimated evaluation value on the display unit 20. For example, the image quality evaluation unit 26 calculates each of the individual evaluation value and the overall evaluation value as the estimated evaluation value.

"Score: 100" in FIG. 3 is an overall evaluation value as an estimated evaluation value calculated by changing the image quality parameter. A graph 54 is a graph representing each individual evaluation value as the estimated evaluation value. A graph 54*a* is an individual evaluation value as an estimated evaluation value of the evaluation item "Resolution". A graph 54*b* is an individual evaluation value as an estimated evaluation value of the evaluation item "Contrast".

Hereinafter, the calculation of the estimated evaluation value will be described.

The image quality evaluation unit 26 changes one or a plurality of image quality parameters associated with each evaluation item by a certain value in the change direction. The image generation unit 16 generates the ultrasound image based on the reception frame output from the transmission/reception unit 14 according to each image quality parameter after the change. The image quality evaluation unit 26 calculates the individual evaluation value and the overall evaluation value for the ultrasound image after each image quality parameter is changed. In this manner, the image quality evaluation unit 26 re-evaluates the image quality of the ultrasound image after each image quality parameter to be changed is changed. The image quality evaluation unit 26 may change each image quality parameter to be changed by a certain value a plurality of times and may re-evaluate the image quality of the ultrasound image a plurality of times. For example, the image quality evaluation unit 26 creates a plurality of conditions by generating a plurality of image quality parameters that are changed by a certain value for each image quality parameter to be changed. The image generation unit 16 generates the ultrasound image under each condition, and the image quality evaluation unit 26 evaluates the image quality of the ultrasound image generated under each condition.

For example, in a case where the individual evaluation value for the evaluation item "Contrast" is lower than the overall evaluation value S, the image quality evaluation unit 26 generates a plurality of conditions by generating five different values for each of the image quality parameters "gain" and "NoiseRed" associated with the evaluation item "Contrast". The image generation unit 16 generates the ultrasound image under each condition. The image quality evaluation unit 26 evaluates the image quality of the ultrasound image generated under each condition. The image quality evaluation unit 26 specifies one or a plurality of image quality parameters for which the individual evaluation value for an evaluation item (for example, spatial resolution or SNR) other than the evaluation item "Contrast" does not decrease, and the individual evaluation value for the evaluation item "Contrast" increases, and specifies a value of the specified one or plurality of image quality parameters.

The notification unit 30 may display the specified one or plurality of image quality parameters as a recommended parameter on the screen 34. In addition, the notification unit 30 may display the value of the specified one or plurality of image quality parameters as a recommended value on the screen 34.

The notification unit 30 displays the evaluation value (for example, the individual evaluation value and the overall evaluation value) of the image quality of the ultrasound image generated according to the recommended value as the estimated evaluation value on the screen 34.

According to Example 1-5, the user can easily understand a relevance between the change direction of the image quality parameter and the estimated evaluation value (that is, the corrected evaluation value). As a result, it is easy for the user to adjust the image quality. In addition, in a case where the recommended value is presented to the user, for example by being displayed on the screen 34, the user can adjust the image quality with reference to the recommended value.

Example 1-6

Figure 4:
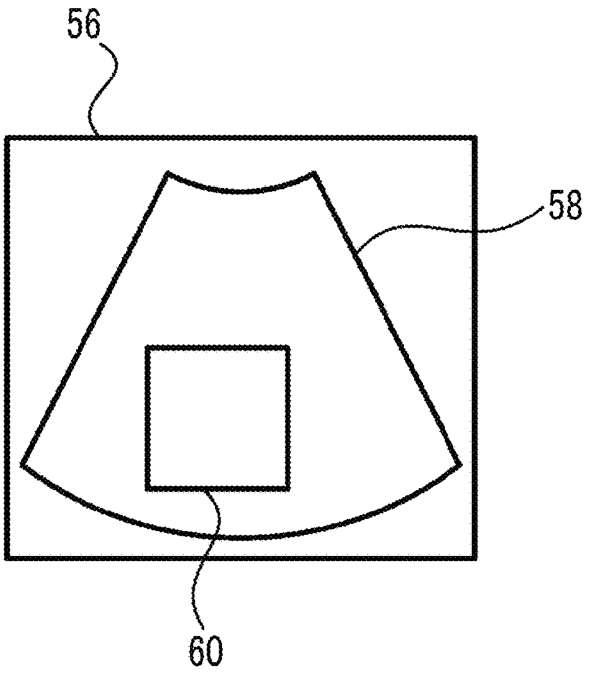
FIG. 4 is a diagram showing an ultrasound image and a region of interest.

Example 1-6 will be described with reference to FIG. 4. FIG. 4 is a diagram showing an ultrasound image and a region of interest (ROI).

In Example 1-6, the image quality evaluation unit 26 calculates the evaluation value based on the reception signal included in the region of interest (ROI). For example, as shown in FIG. 4, a screen 56 is displayed on the display unit 20. An ultrasound image 58 (for example, a B-mode image) generated by the transmission and reception of the ultrasound waves is displayed on the screen 56. In a case where the user designates a region of interest 60 on the ultrasound image 58 by using the operation unit 22, the image quality evaluation unit 26 evaluates an image quality of an image in the designated region of interest 60. That is, the image quality evaluation unit 26 calculates the individual evaluation value and the overall evaluation value of the image in the region of interest 60.

Also in Example 1-6, the processing according to Example 1-1 to Example 1-5 described above is executed. For example, the image quality parameter for increasing the evaluation value (for example, the individual evaluation value and the overall evaluation value) calculated from the image in the region of interest is specified, and the specified image quality parameter and information indicating a change direction of the image quality parameter are notified to the user.

According to Example 1-6, it is possible to change the image quality parameter in a manner specialized for the region of interest of the user.

Example 1-7

In Example 1-7, as described above, a plurality of evaluation items for evaluating the image quality of the ultrasound image are predetermined. The image quality evaluation unit 26 calculates an individual evaluation value for an evaluation item selected by the user from among the plurality of evaluation items. The notification unit 30 notifies the user of the calculated individual evaluation value by, for example, displaying the individual evaluation value on the display unit 20.

In addition, the image quality evaluation unit 26 specifies one or a plurality of image quality parameters for increasing the individual evaluation value for each evaluation item and the change direction of each image quality parameter. This specifying method is the same as a specifying method according to Example 1-1 described above.

The image generation unit 16 generates the ultrasound image according to the changed image quality parameter for increasing the individual evaluation value for each evaluation item. That is, the change direction of the image quality parameter for increasing the individual evaluation value is specified by the image quality evaluation unit 26, and the image generation unit 16 changes the image quality parameter by a certain value in the change direction and generates the ultrasound image according to a value after the change. The notification unit 30 displays the generated ultrasound image on the display unit 20.

Figure 5:
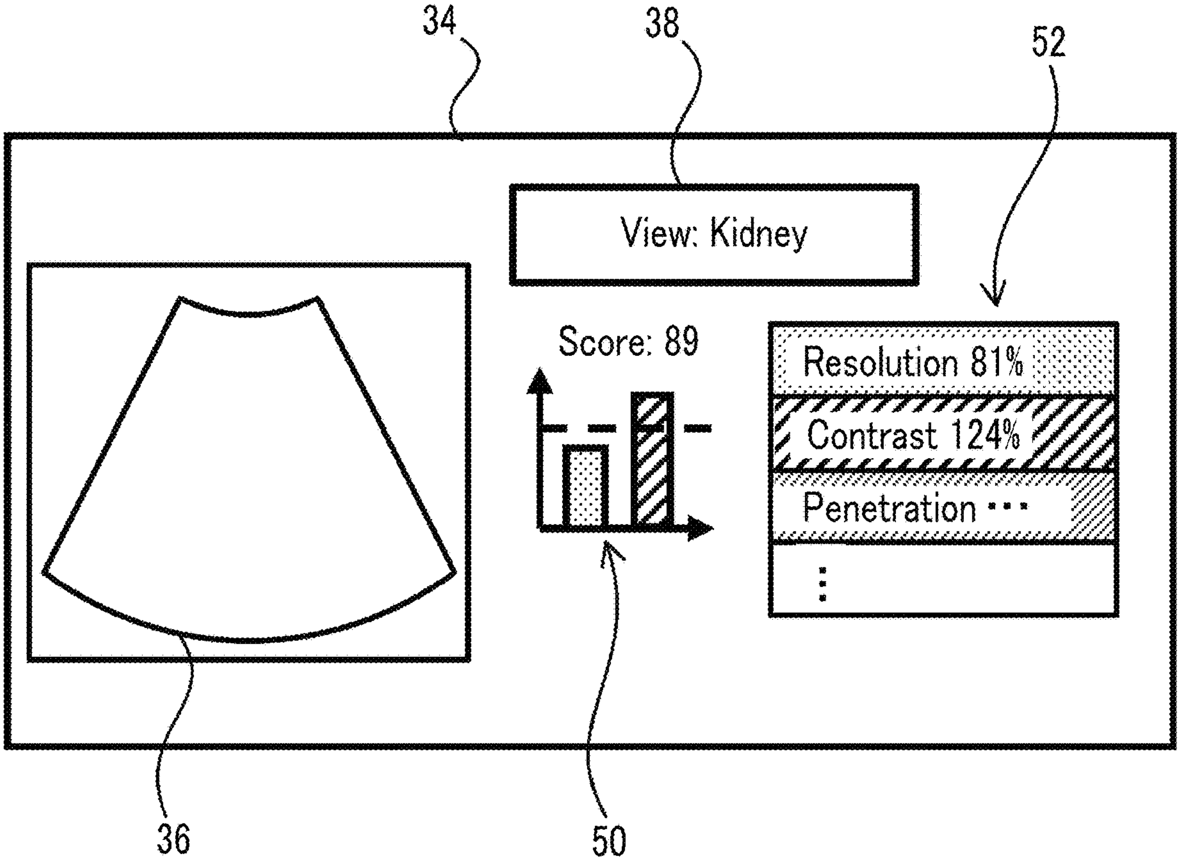
FIG. 5 is a diagram showing a screen displaying an evaluation value and an image quality parameter.
Figure 6:
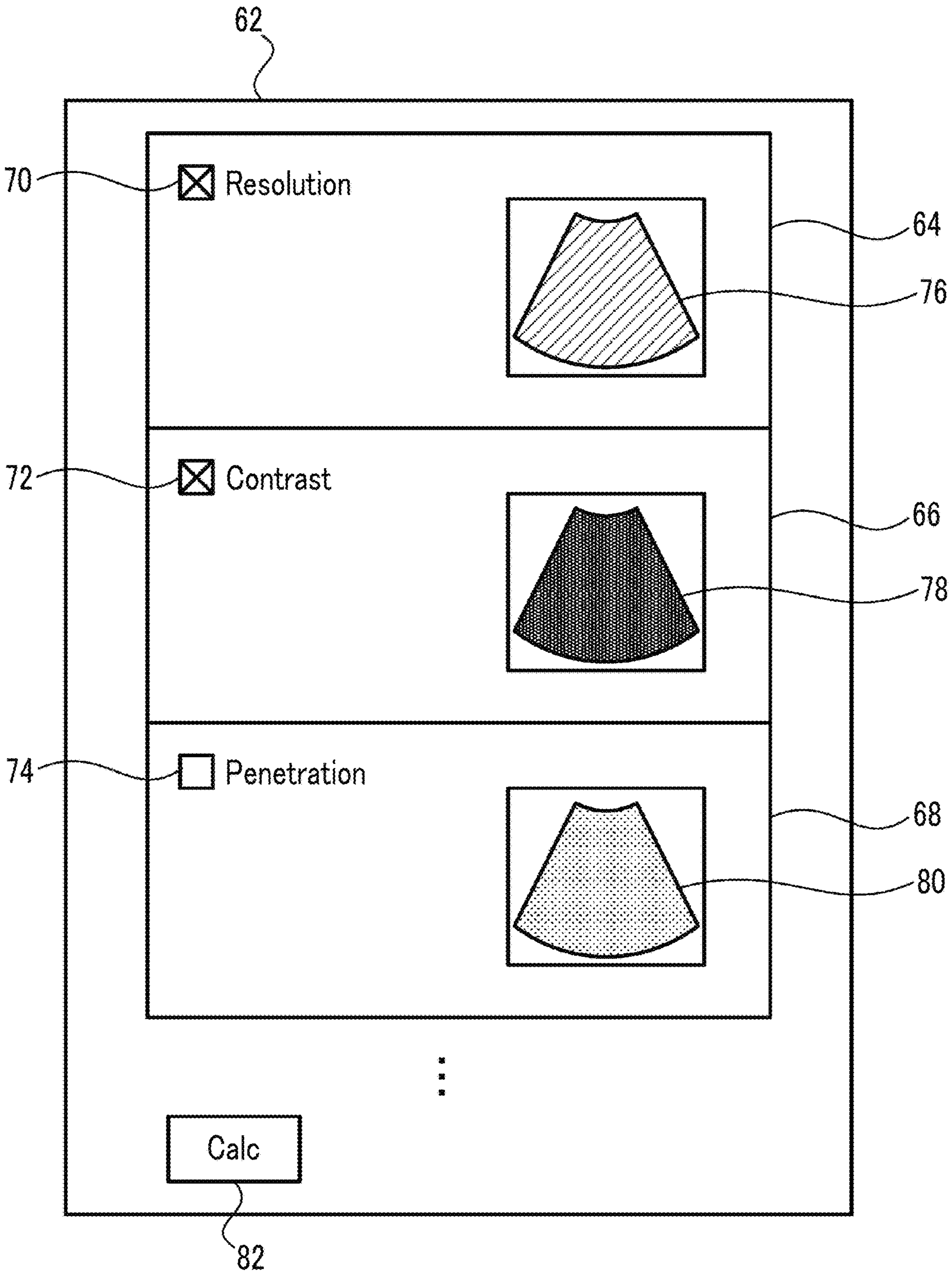
FIG. 6 is a diagram showing a screen for selecting an evaluation item.

Hereinafter, Example 1-7 will be described with reference to FIGS. 5 and 6. FIG. 5 shows a screen 34 displaying an evaluation value and an image quality parameter. FIG. 6 shows a selection screen 62 for selecting the evaluation item.

In a case where the ultrasound image is generated and the image quality is evaluated, as shown in FIG. 5, the ultrasound image 36, the diagnostic site information (see the reference numeral 38), the list 52 of the individual evaluation values, and the graph 50 are displayed on the screen 34. The contents shown in FIG. 5 are the same as a part of the contents shown in FIG. 3.

For example, an image (for example, an icon or a button image) for giving an instruction to display the selection screen 62 is displayed on the display unit 20. In a case where the user gives an instruction to display the selection screen 62 by, for example, pressing the image using the operation unit 22, the notification unit 30 displays the selection screen 62 on the display unit 20.

The notification unit 30 displays selection regions 64, 66, 68, . . . on the selection screen 62. Each selection region is a region for the user to select an evaluation item. For example, the selection region 64 is a region for selecting the evaluation item "Resolution". The selection region 66 is a region for selecting the evaluation item "Contrast". The selection region 68 is a region for selecting the evaluation item "Penetration".

A check box 70 is displayed in the selection region 64. The user can select the evaluation item "Resolution" by checking (that is, by clicking) the check box 70 on the selection screen 62. The user can cancel the selection of the evaluation item "Resolution" by unchecking (that is, by unclicking) the check box 70 on the selection screen 62.

Similarly, a check box 72 is displayed in the selection region 66, and a check box 74 is displayed in the selection region 68. The user can select the evaluation item "Contrast" or cancel the selection by operating the check box 72. The user can select the evaluation item "Penetration" or cancel the selection by operating the check box 74.

In the example shown in FIG. 6, the evaluation item "Resolution" and the evaluation item "Contrast" are selected by the user, and the evaluation item "Penetration" is not selected. In this case, the image quality evaluation unit 26 calculates an individual evaluation value for each of the evaluation item "Resolution" and the evaluation item "Contrast". In addition, the image quality evaluation unit 26 calculates an overall evaluation value based on the individual evaluation values for each of the evaluation item "Resolution" and the evaluation item "Contrast". The notification unit 30 displays the overall evaluation value and the individual evaluation value for each of the evaluation item "Resolution" and the evaluation item "Contrast" on the screen 34.

In addition, the image quality evaluation unit 26 specifies one or a plurality of image quality parameters for increasing the individual evaluation value for each of the evaluation items "Resolution", "Contrast", "Penetration", . . . , and a change direction of each image quality parameter. The image generation unit 16 generates the ultrasound image according to the changed image quality parameter for increasing the individual evaluation value for each of the evaluation items "Resolution", "Contrast", "Penetration", and the like. The notification unit 30 displays the generated ultrasound image on the selection screen 62.

For example, an ultrasound image 76 is an ultrasound image generated according to one or a plurality of changed image quality parameters for increasing the individual evaluation value for the evaluation item "Resolution", and is displayed in the selection region 64. An ultrasound image 78 is an ultrasound image generated according to one or a plurality of changed image quality parameters for increasing the individual evaluation value for the evaluation item "Contrast", and is displayed in the selection region 66. An ultrasound image 80 is an ultrasound image generated according to one or a plurality of changed image quality parameters for increasing the individual evaluation value for the evaluation item "Penetration", and is displayed in the selection region 68. The ultrasound images 76, 78, and 80 are sample images that have been adjusted from the viewpoint of each evaluation item. The user can select the evaluation item with reference to the ultrasound images 76, 78, and 80.

In addition, an image 82, such as an icon or a button image, may be displayed on the selection screen 62. The image 82 is an image for the user to give an instruction to evaluate the image quality. For example, in a case where the user selects the evaluation item on the selection screen 62 and presses the image 82, the image quality evaluation unit 26 calculates the individual evaluation value and the overall evaluation value for the evaluation item selected by the user, and the notification unit 30 displays the calculated individual evaluation value and overall evaluation value on the screen 34.

The user may select the evaluation item before an individual evaluation value and an overall evaluation value for a default evaluation item set in advance are calculated, or may select the evaluation item after the individual evaluation value and the overall evaluation value for the default evaluation item set in advance are calculated.

According to Example 1-7, it is easy to change the image quality parameter related to the evaluation item desired by the user.

Example 1-8

In Example 1-8, the image quality evaluation unit 26 calculates a recommended value of the image quality parameter for increasing the evaluation value. For example, as described in Example 1-5 above, the image quality evaluation unit 26 specifies one or a plurality of recommended parameters and recommended values. The notification unit 30 notifies the user of the recommended value by, for example, displaying the recommended value on the display unit 20.

Figure 7:
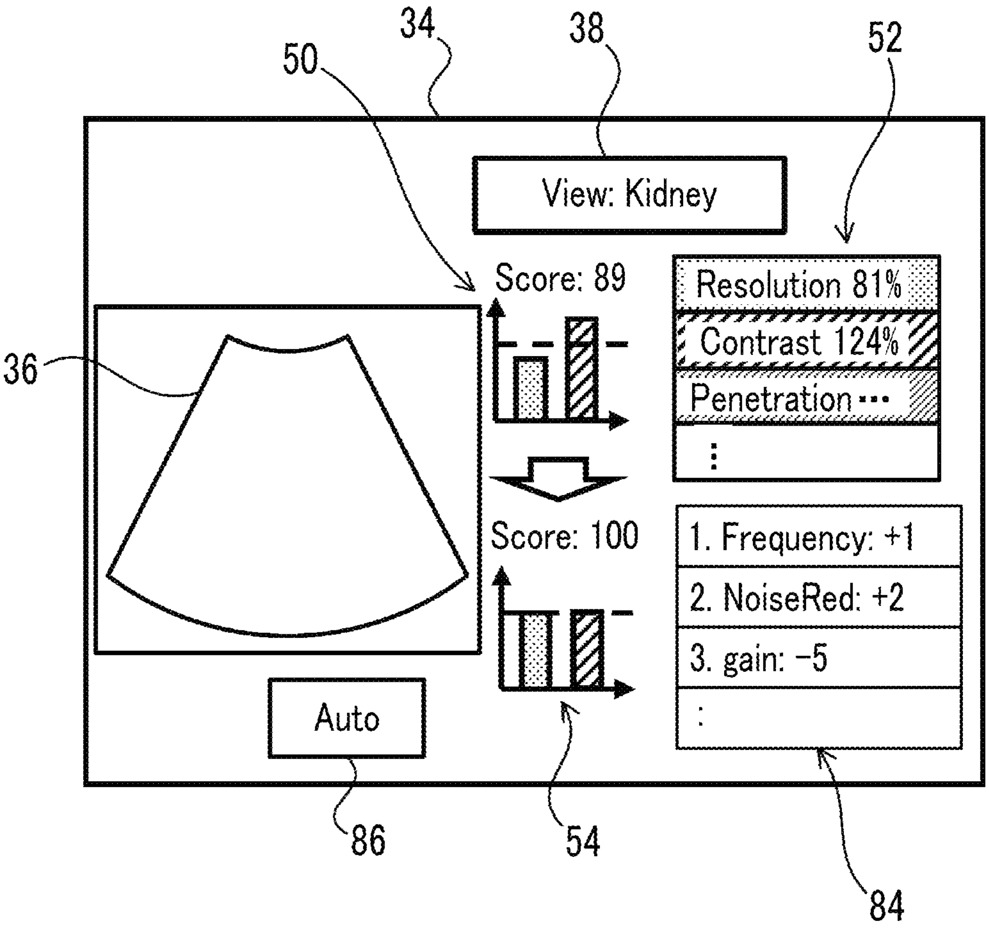
FIG. 7 is a diagram showing a screen for displaying an evaluation value and an image quality parameter.

FIG. 7 shows a display example of the recommended value. For example, in a case where the ultrasound image is generated and the image quality is evaluated, the ultrasound image 36, the diagnostic site information (see the reference numeral 38), the list 52 of individual evaluation values, the graphs 50 and 54, and a list 84 of image quality parameters to be changed are displayed on the screen 34. In the list 84 of the image quality parameters to be changed, "transmission frequency" ("Frequency" in FIG. 7), "the number of frames to be smoothed" ("NoiseRed" in FIG. 7), and "gain" are specified as the image quality parameters to be changed, as in the list 42 shown in FIGS. 2 and 3.

In addition, a recommended value "+1" is calculated as the recommended value of the image quality parameter "transmission frequency" and is displayed in a display region of the image quality parameter "transmission frequency" in the list 84. A recommended value "+2" is calculated as the recommended value of the image quality parameter "the number of frames to be smoothed" and is displayed in a display region of the image quality parameter "the number of frames to be smoothed" in the list 84. A recommended value "−5" is calculated as the recommended value of the image quality parameter "gain", and is displayed in a display region of the image quality parameter "gain" in the list 84. The user can change a value of each image quality parameter with reference to these recommended values.

According to Example 1-8, since the recommended value is notified to the user, the user can change the value of the image quality parameter with reference to the recommended value. Therefore, it is possible to reduce a time and effort of an operation of the user.

In addition, an image 86, such as an icon or a button image, may be displayed on the screen 34. The image 86 is an image for allowing the user to give an instruction to automatically switch the value of each image quality parameter to the recommended value. In a case where the user presses the image 86, the image generation unit 16 automatically switches the value of each image quality parameter to the recommended value and generates the ultrasound image according to the recommended value of each image quality parameter. In this manner, a recommended ultrasound image is generated without the user manually changing the value of each image quality parameter. For example, the ultrasound image is displayed on the screen 34.

Second Embodiment

Figure 8:
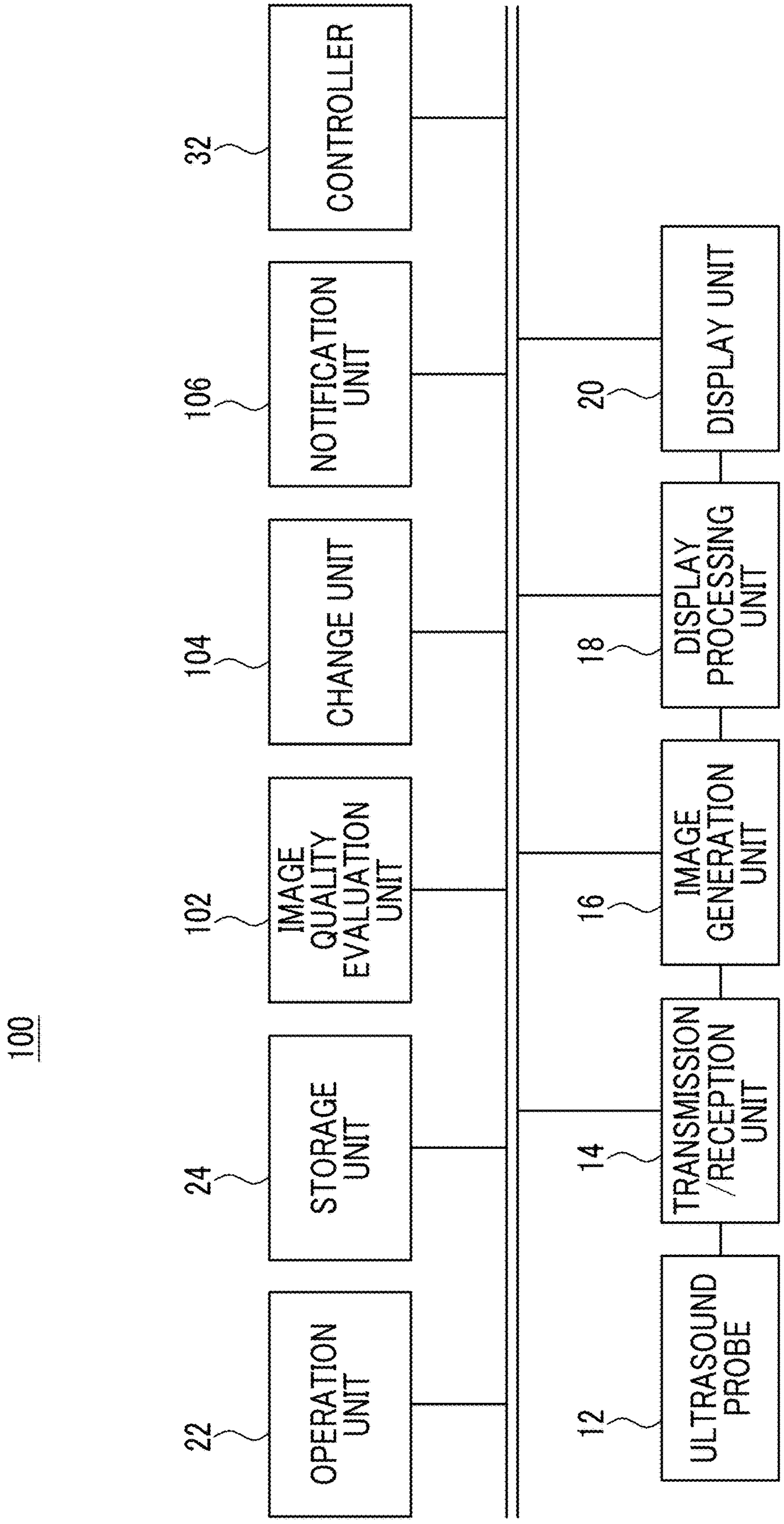
FIG. 8 is a block diagram showing a configuration of an ultrasound diagnostic apparatus according to a second embodiment.

An ultrasound diagnostic apparatus 100 according to a second embodiment will be described with reference to FIG. 8. FIG. 8 is a block diagram showing an example of a configuration of the ultrasound diagnostic apparatus 100 according to the second embodiment.

Similarly to the ultrasound diagnostic apparatus 10 according to the first embodiment, the ultrasound diagnostic apparatus 100 includes the ultrasound probe 12, the transmission/reception unit 14, the image generation unit 16, the display processing unit 18, the display unit 20, the operation unit 22, the storage unit 24, and the controller 32. The configurations and functions thereof are the same as those of the first embodiment.

In addition, the ultrasound diagnostic apparatus 100 includes an image quality evaluation unit 102, a change unit 104, and a notification unit 106. The image quality evaluation unit 102 evaluates the image quality of the ultrasound image generated by the image generation unit 16. The change unit 104 changes the image quality parameter. The notification unit 106 notifies the user of various types of information.

Hereinafter, each example according to the second embodiment will be described.

Example 2-1

Hereinafter, Example 2-1 will be described.

The image quality evaluation unit 102 evaluates the image quality of the ultrasound image generated by the image generation unit 16. The image quality evaluation unit 102 may evaluate the image quality of the ultrasound image based on the ultrasound image output from the image generation unit 16, or may evaluate the image quality of the ultrasound image based on the reception signal or the reception frame. In the following, as an example, the image quality evaluation unit 102 evaluates the image quality of the ultrasound image based on the ultrasound image output from the image generation unit 16. The image quality evaluation unit 102 corresponds to an example of a calculation unit.

The image quality evaluation unit 102 may evaluate the image quality of the ultrasound image by the same processing as the processing by the image quality evaluation unit 26 according to the first embodiment. For example, the image quality evaluation unit 102 may calculate an individual evaluation value for each evaluation item (for example, spatial resolution, contrast, SNR, and the like) and calculate an overall evaluation value based on a plurality of the individual evaluation values.

As another example, the image quality evaluation unit 102 may evaluate the image quality of the ultrasound image based on a combination of a plurality of quantitative values such as a frequency component, an average brightness value, and a brightness distribution of the ultrasound image, or may evaluate the image quality of the ultrasound image based on an analysis algorithm using the quantitative values as feature amounts.

As still another example, the image quality evaluation unit 102 may evaluate the image quality of the ultrasound image using a machine learning algorithm. The machine learning algorithm is an algorithm that has been trained in advance using an ultrasound image with a high evaluation value as a training image, and is an algorithm that determines an ultrasound image with a high evaluation value.

In the second embodiment, the image generation unit 16 generates a first ultrasound image according to a first image quality parameter. For example, the first image quality parameter is an image quality parameter determined in advance or an image quality parameter designated by the user. As in the first embodiment, the image quality parameter is a transmission frequency, the number of frames to be smoothed, a gain, a transmission focus, a scan line density, a dynamic range, a brightness gamma curve, the number of compounds, and the like.

In a case where the first ultrasound image is generated, the image quality evaluation unit 102 calculates a first evaluation value indicating an evaluation of an image quality of the first ultrasound image. For example, the overall evaluation value is calculated as the first evaluation value.

The change unit 104 generates a second image quality parameter different from the first image quality parameter by changing the image quality parameter. For example, in a case where the first evaluation value is equal to or less than a predetermined threshold value, the change unit 104 generates the second image quality parameter by changing the image quality parameter. For example, the change unit 104 generates the second image quality parameter by changing the image quality parameter according to a multivariate function. As described in the first embodiment, the change unit 104 may calculate the recommended value of the image quality parameter and may set the calculated recommended value as the second image quality parameter.

The change unit 104 gives an instruction to change the image quality parameter to the image generation unit 16. The image generation unit 16 generates a second ultrasound image according to the image quality parameter (that is, the second image quality parameter) changed by the change unit 104. Depending on the type of the image quality parameter, the change unit 104 gives an instruction to change the image quality parameter to the transmission/reception unit 14. The transmission/reception unit 14 performs the transmission and reception of the ultrasound waves according to the image quality parameter (that is, the second image quality parameter) changed by the change unit 104. As a result, a reception signal corresponding to the second image quality parameter is received by the transmission/reception unit 14.

For example, a gain, a dynamic range, a brightness gamma curve, and the number of compounds are image quality parameters related to the image generation unit 16. The change unit 104 changes these image quality parameters to generate a plurality of second image quality parameters for the image generation unit 16. The image generation unit 16 generates the second ultrasound image according to the plurality of second image parameters.

Further, for example, the transmission focus, the scan line density, and the frequency are image quality parameters related to the transmission/reception unit 14. The change unit 104 changes these image quality parameters to generate a plurality of second image quality parameters for the transmission/reception unit 14. The transmission/reception unit 14 transmits and receives ultrasound waves according to the plurality of second image parameters to receive reception signals corresponding to the plurality of second image parameters. The reception signals are processed by the transmission/reception unit 14, so that reception frames corresponding to the plurality of second image parameters are generated and output to the image generation unit 16. The image generation unit 16 generates the second ultrasound image based on the reception frames.

The change unit 104 may give an instruction to change the image quality parameter to only the image generation unit 16, may give an instruction to change the image quality parameter to both the transmission/reception unit 14 and the image generation unit 16, or may give an instruction to change the image quality parameter to only the transmission/reception unit 14.

In a case where the second ultrasound image is generated, the image quality evaluation unit 102 calculates a second evaluation value indicating an evaluation of an image quality of the second ultrasound image. For example, the overall evaluation value is calculated as the second evaluation value.

The notification unit 106 notifies the user of various types of information. For example, the notification unit 106 may display various types of information on the display unit 20 or may output various types of information as audio information from a speaker.

In the second embodiment, in a case where the second evaluation value is equal to or less than a predetermined threshold value, the notification unit 106 notifies the user of a fact that the evaluation value of the image quality of the ultrasound image does not exceed the threshold value even though the image quality parameter is changed. For example, the notification unit 106 may display a message indicating the above fact on the display unit 20 or may display an image indicating the above fact on the display unit 20. Specifically, the notification unit 106 displays a message that "A score is low. The score does not increase even in a case where the image quality parameter is changed" on the display unit 20. In addition, the notification unit 106 displays a red image representing that the evaluation value does not exceed the threshold value on the display unit 20.

For example, the change unit 104 sequentially generates a plurality of second image quality parameters different from each other by sequentially changing each image quality parameter according to the multivariate function described above. Each time the change is made, the transmission/reception unit 14 transmits and receives the ultrasound waves according to the second image quality parameter, and the image generation unit 16 generates the second ultrasound image according to the second image quality parameter. By changing the image quality parameter a plurality of times, a plurality of second ultrasound images corresponding to the number of times the image quality parameter is changed are generated. The image quality evaluation unit 102 calculates a second evaluation value indicating an evaluation of an image quality of each of the plurality of second ultrasound images. In this way, a transition of the second evaluation value is obtained.

For example, in a case where the second evaluation value is not equal to or greater than the threshold value even though the image quality parameter is changed a predetermined number of times, the notification unit 106 may notify the user that the evaluation value of the image quality of the ultrasound image does not exceed the threshold value even though the image quality parameter is changed.

In a case where the second evaluation value is equal to or greater than the threshold value, the notification unit 106 may display a message indicating that the evaluation of the image quality is high on the display unit 20, or may display an image (for example, a blue image) indicating that the evaluation of the image quality is high on the display unit 20. In a case where the second evaluation value is equal to or greater than the threshold value, the notification unit 106 may not display the message or the image on the display unit 20. The fact that the second evaluation value is equal to or greater than the threshold value means that there is room for improving the image quality of the ultrasound image by changing the image quality parameter.

As described above, according to the second embodiment, it is possible to reduce a time for trial and error of the user for adjusting the image quality of the ultrasound image. That is, even though the image quality of the ultrasound image cannot be improved by changing the image quality parameter (that is, even though the second evaluation value is not equal to or greater than the threshold value), manually adjusting the image quality parameter multiple times by the user may result in an increase in entire examination time. According to the second embodiment, the user is notified that the evaluation value of the image quality of the ultrasound image does not exceed the threshold value even though the image quality parameter is changed. Therefore, the user does not need to spend a time and effort to adjust the image quality of the ultrasound image. For example, it is considered that the user reduces a time required for adjusting the image quality of the ultrasound image by replacing the ultrasound probe 12 with another ultrasound probe 12 or executing a next examination first without changing the image quality parameter. In this manner, a total time for the ultrasound examination can be shortened.

Example 2-2

In Example 2-2, the threshold value described in Example 2-1 is determined for each subject. The notification unit 106 notifies the user that the evaluation value of the image quality of the ultrasound image does not exceed the threshold value even though the image quality parameter is changed by changing the threshold value for each subject where the ultrasound waves are transmitted and received.

Figure 9:
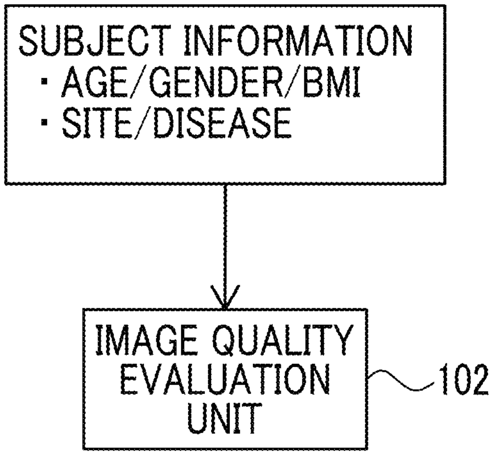
FIG. 9 is a block diagram for describing subject information and an image quality evaluation unit.

Example 2-2 will be described in detail with reference to FIG. 9. FIG. 9 is a block diagram for describing subject information and the image quality evaluation unit 102.

The subject information is information indicating an attribute of the subject. For example, the attribute of the subject is an age, a gender, a BMI value, a diagnostic site, a disease, and the like of the subject. A specific example thereof is that the subject has an attribute of 30*s*, a male, a BMI value of 20, and a liver. The subject information is input to the image quality evaluation unit 102. For example, the user may input the subject information related to the subject to be examined to the ultrasound diagnostic apparatus 100 by using the operation unit 22, or the subject information may be input to the ultrasound diagnostic apparatus 100 via a communication path, such as a network.

A different threshold value is determined for each attribute of the subject indicated by the subject information, and the threshold value corresponding to the attribute is stored in the storage unit 24 in advance. The image quality evaluation unit 102 acquires the threshold value corresponding to the attribute of the subject indicated by the input subject information from the storage unit 24. The image quality evaluation unit 102 compares the calculated first evaluation value with the threshold value. In a case where the second ultrasound image is generated and the second evaluation value is calculated because the first evaluation value is equal to or less than the threshold value, the image quality evaluation unit 102 compares the second evaluation value with the threshold value. In a case where the second evaluation value is equal to or less than the threshold value, the notification unit 106 notifies the user that the evaluation value of the image quality of the ultrasound image does not exceed the threshold value even though the image quality parameter is changed.

According to Example 2-2, since the image quality of the ultrasound image can be evaluated according to the threshold value corresponding to the attribute of the subject, an accuracy of the evaluation can be improved.

Example 2-3

In Example 2-3, the image quality evaluation unit 102 may calculate the first evaluation value and the second evaluation value in real time during the transmission and reception of the ultrasound waves. The change unit 104 may change the image quality parameter in real time during the transmission and reception of the ultrasound waves. That is, in Example 2-3, the generation of the first ultrasound image, the calculation of the first evaluation value, the change of the image quality parameter, the generation of the second ultrasound image, and the calculation of the second evaluation value may be performed in real time during the transmission and reception of the ultrasound waves.

As another example, the generation of the first ultrasound image, the calculation of the first evaluation value, the change of the image quality parameter, the generation of the second ultrasound image, and the calculation of the second evaluation value may be performed after the ultrasound images of a predetermined number of frames are acquired.

As still another example, the generation of the first ultrasound image, the calculation of the first evaluation value, the change of the image quality parameter, the generation of the second ultrasound image, and the calculation of the second evaluation value may be performed after a predetermined time has elapsed from a certain point in time (for example, an imaging start point in time).

For example, by evaluating the image quality and changing the image quality parameter in real time, even in a case where a location (for example, a cross section) where the ultrasound waves are transmitted and received are changed, the image quality can be evaluated following the change. As a result, the user can easily associate the operation of the ultrasound probe 12 with the evaluation value, and can quickly decide how to operate the ultrasound probe 12 (for example, how to press the ultrasound probe 12).

Example 2-4

In Example 2-4, in a case where there is an instruction from the user, the image quality evaluation unit 102 evaluates the ultrasound image, and the change unit 104 changes the image quality parameter. The user can give the instruction to the image quality evaluation unit 102 and the change unit 104 by operating the operation unit 22. An image (for example, an icon or a button image) for giving the instruction may be displayed on the display unit 20, and the user may give the instruction to the image quality evaluation unit 102 and the change unit 104 by, for example, pressing the image.

For example, the image quality evaluation unit 102 may evaluate the ultrasound image in real time until the user gives an instruction to stop the evaluation, or may evaluate the ultrasound image in a case where the user gives an instruction to perform the evaluation. Similarly, the change unit 104 may change the image quality parameter in real time until the user gives an instruction to stop the change, or may change the image quality parameter in a case where the user gives an instruction to perform the change.

According to Example 2-4, since the evaluation of the image quality and the change of the image quality parameter are performed at a timing desired by the user, unnecessary notification is not given to the user.

Example 2-5

Figure 10:
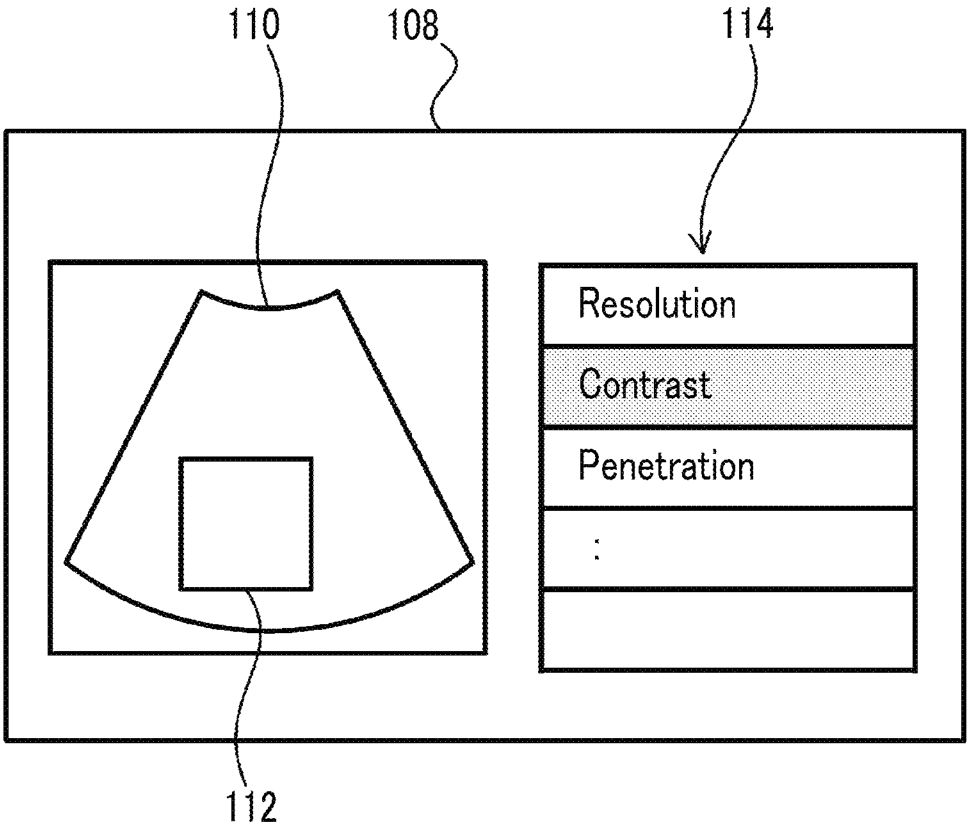
FIG. 10 is a diagram showing an ultrasound image and a region of interest.

Example 2-5 will be described with reference to FIG. 10. FIG. 10 is a diagram showing an ultrasound image and a region of interest (ROI).

In Example 2-5, the image quality evaluation unit 102 calculates the first evaluation value and the second evaluation value based on an image included in a region of interest (ROI) set in the ultrasound image. For example, as shown in FIG. 10, a screen 108 is displayed on the display unit 20. An ultrasound image 110 (for example, a B-mode image) generated by the transmission and reception of the ultrasound waves is displayed on the screen 108. In a case where the user designates a region of interest 112 on the ultrasound image 110 using the operation unit 22, the image quality evaluation unit 102 evaluates an image quality of an image in the designated region of interest 112. That is, the image quality evaluation unit 102 calculates the first evaluation value and the second evaluation value of the image in the region of interest 112.

Also in Example 2-5, the processing related to Example 2-1 to Example 2-4 described above is executed. For example, in a case where the first evaluation value is equal to or less than the threshold value, the image quality parameter is changed to generate the second ultrasound image, and the second evaluation value is calculated based on the second ultrasound image. In a case where the second evaluation value is equal to or less than the threshold value, the user is notified that the evaluation value does not exceed the threshold value even though the image quality parameter is changed.

According to Example 2-5, since the image quality of the image included in the region of interest of the user is evaluated, unnecessary notification is not given to the user.

In addition, in Example 2-5, a plurality of evaluation items for evaluating the image quality of the ultrasound image are predetermined. The image quality evaluation unit 102 calculates a first individual evaluation value for an evaluation item selected by the user from among the plurality of evaluation items based on the first ultrasound image, and calculates a second individual evaluation value for an evaluation item selected by the user from among the plurality of evaluation items based on the second ultrasound image. In a case where the first individual evaluation value is equal to or less than the threshold value, the change unit 104 changes the image quality parameter. As a result, the second ultrasound image is generated. In a case where the second individual evaluation value is equal to or less than the threshold value, the notification unit 106 notifies the user that the evaluation value of the image quality of the ultrasound image does not exceed the threshold value even though the image quality parameter is changed.

For example, as shown in FIG. 10, a list 114 of evaluation items is displayed on the screen 108. In a case where the user selects the evaluation item on the screen 108, the image quality evaluation unit 102 calculates a first individual evaluation value for the selected evaluation item based on the first ultrasound image, and calculates a second individual evaluation value for the selected evaluation item based on the second ultrasound image.

In a case where the second individual evaluation value is equal to or less than the threshold value, the notification unit 106 notifies the user that the evaluation value does not exceed the threshold value even though the image quality parameter is changed, as in Example 2-1 to Example 2-4 described above.

In addition, in a case where a plurality of evaluation items are selected by the user, the image quality evaluation unit 102 calculates a first individual evaluation value of each of the selected plurality of evaluation items based on the first ultrasound image, and calculates an overall evaluation value based on a plurality of the first individual evaluation values. In a case where the overall evaluation value calculated based on the plurality of first individual evaluation values is equal to or less than the threshold value, the change unit 104 changes the image quality parameter. The image quality evaluation unit 102 calculates a second individual evaluation value of each of the plurality of evaluation items selected by the user based on the second ultrasound image generated according to the changed image quality parameter, and calculates an overall evaluation value based on a plurality of the second individual evaluation values. In a case where the overall evaluation value calculated based on the plurality of second individual evaluation values is equal to or less than the threshold value, the notification unit 106 notifies the user that the evaluation value does not exceed the threshold value even though the image quality parameter is changed.

As described above, the ultrasound image is evaluated from a viewpoint of evaluation desired by the user by evaluating the ultrasound image for one or a plurality of evaluation items selected by the user. As a result, unnecessary notification is not given to the user.

Example 2-6

In Example 2-6, the evaluation value and the image quality parameter to be changed for increasing the evaluation value are associated with each other in advance. The evaluation value here may be an overall evaluation value or an individual evaluation value. In the following, the overall evaluation value will be described as an example.

In a case where a first evaluation value (for example, an overall evaluation value) is calculated, the change unit 104 specifies a combination of the image quality parameters associated with the first evaluation value. For example, the change unit 104 specifies a combination of the image quality parameters associated with the first evaluation value by using a machine learning algorithm. The machine learning algorithm is an algorithm that has learned the overall evaluation and a combination of the image quality parameters to be changed for increasing the overall evaluation value in advance, and is an algorithm that specifies a combination of the image quality parameters for increasing the overall evaluation value.

The image generation unit 16 generates the second ultrasound image according to the combination of the image quality parameters specified by the change unit 104.

According to Example 2-6, since the image quality parameter for increasing the evaluation value is automatically determined, it is possible to efficiently change the image quality parameter.

The image generation unit 16, the display processing unit 18, the image quality evaluation unit 26 or 102, the site information acquisition unit 28, the notification unit 30 or 106, the change unit 104, and the controller 32 can be realized by using hardware resources such as a processor or an electronic circuit, and a device such as a memory may be used as necessary in the realization. In addition, the image generation unit 16, the display processing unit 18, the image quality evaluation unit 26 or 102, the site information acquisition unit 28, the notification unit 30 or 106, the change unit 104, and the controller 32 may be realized by, for example, a computer. That is, all or some of the image generation unit 16, the display processing unit 18, the image quality evaluation unit 26 or 102, the site information acquisition unit 28, the notification units 30 or 106, the change unit 104, and the controller 32 may be realized by cooperation between hardware resources such as a central processing unit (CPU) and a memory provided in the computer and software (program) that defines an operation of the CPU and the like. The program is stored in the storage unit 24 of the ultrasound diagnostic apparatus 10 or 100 or other storage devices through a recording medium, such as a CD or a DVD, or a communication path, such as a network. As another example, the image generation unit 16, the display processing unit 18, the image quality evaluation unit 26 or 102, the site information acquisition unit 28, the notification unit 30 or 106, the change unit 104, and the controller 32 may be realized by a digital signal processor (DSP), an application specific integrated circuit (ASIC), afield programmable gate array (FPGA), or the like. Of course, a graphics processing unit (GPU) and the like may be used. The image generation unit 16, the display processing unit 18, the image quality evaluation unit 26 or 102, the site information acquisition unit 28, the notification unit 30 or 106, the change unit 104, and the controller 32 may be realized by a single device or may be realized by a plurality of devices.

In addition, functions of each of the image generation unit 16, the display processing unit 18, the image quality evaluation unit 26 or 102, the site information acquisition unit 28, the notification unit 30 or 106, and the change unit 104 may be executed by a device (for example, a personal computer or a server) other than the ultrasound diagnostic apparatus 10 or 100.

What is claimed is:

1. An ultrasound diagnostic apparatus comprising:

one or more processors, the one or more processors configured to:

calculate based on a reception signal acquired by transmission and reception of ultrasound waves, an individual evaluation value indicating an evaluation of an image quality of an ultrasound image generated based on the reception signal, for each of a plurality of evaluation items for evaluating the image quality of the ultrasound image, and calculate an overall evaluation value based on a plurality of the individual evaluation values;

notify a user of an image quality parameter for adjusting the image quality of the ultrasound image; and notify the user of the image quality parameter for increasing the overall evaluation value, wherein the image quality parameter is related to an individual evaluation value among the plurality of individual evaluation values, which is lower than the overall evaluation value, wherein the evaluation item includes a contrast, a spatial resolution, or an SNR of the ultrasound image, and the image quality parameter includes at least one of a transmission frequency, a number of frames to be smoothed, a gain, a transmission focus, a scan line density, a dynamic range, a brightness gamma curve, or a number of compounds.

2. The ultrasound diagnostic apparatus according to claim 1, wherein the one or more processors are configured to notify the user of a change direction of the image quality parameter for increasing the overall evaluation value.

3. The ultrasound diagnostic apparatus according to claim 2, wherein an evaluation item for evaluating the image quality of the ultrasound image is determined for each diagnostic site where the ultrasound waves are transmitted and received, a threshold value is predetermined for each diagnostic site, the one or more processors are configured to calculate the individual evaluation value for the evaluation item for evaluating the image quality of the ultrasound image of the diagnostic site where the ultrasound waves are transmitted and received, based on the reception signal, and in a case where the overall evaluation value is equal to or less than the threshold value for the diagnostic site, the one or more processors are configured to notify the user of the change direction of the image quality parameter for increasing the overall evaluation value.

4. The ultrasound diagnostic apparatus according to claim 2, wherein the one or more processors are configured to notify the user of each calculated individual evaluation value.

5. The ultrasound diagnostic apparatus according to claim 4, wherein the one or more processors are configured to calculate the individual evaluation value or the overall evaluation value, which is calculated in a case where the image quality parameter is changed according to the change direction, as an estimated evaluation value, and notify the user of the estimated evaluation value.

6. The ultrasound diagnostic apparatus according to claim 2, wherein the one or more processors are configured to calculate an individual evaluation value for an evaluation item selected by the user from among the plurality of evaluation items, and notify the user of the calculated individual evaluation value.

7. The ultrasound diagnostic apparatus according to claim 6, wherein the one or more processors are configured to display an ultrasound image generated based on a changed image quality parameter for increasing the individual evaluation value for each evaluation item, on a display.

8. The ultrasound diagnostic apparatus according to claim 1, wherein the one or more processors are configured to calculate the overall evaluation value based on the reception signal included in a region of interest.

9. The ultrasound diagnostic apparatus according to claim 1, wherein the one or more processors are configured to calculate a recommended value of the image quality parameter for increasing the overall evaluation value, and notify the user of the recommended value.

10. The ultrasound diagnostic apparatus according to claim 1, wherein the evaluation item includes a contrast, a spatial resolution, and an SNR of the ultrasound image.

11. The ultrasound diagnostic apparatus according to claim 1, wherein the one or more processors are configured to display an individual evaluation value for each evaluation item on a display.

12. The ultrasound diagnostic apparatus according to claim 1, wherein the one or more processors are configured to display an individual evaluation value for each evaluation item and an overall evaluation value on a display.

13. A non-transitory computer-readable storage medium storing a program for causing a computer to execute a process to:

calculate, based on a reception signal acquired by transmission and reception of ultrasound waves, an individual evaluation value indicating an evaluation of an image quality of an ultrasound image generated based on the reception signal, for each of a plurality of evaluation items for evaluating the image quality of the ultrasound image, and calculate an overall evaluation value based on a plurality of the individual evaluation values;

notify a user of an image quality parameter for adjusting the image quality of the ultrasound image; and notify the user of the image quality parameter for increasing the overall evaluation value, wherein the image quality parameter is related to an individual evaluation value among the plurality of individual evaluation values, which is lower than the overall evaluation value, and wherein the evaluation item includes a contrast, a spatial resolution, or an SNR of the ultrasound image, and the image quality parameter includes at least one of a transmission frequency, a number of frames to be smoothed, a gain, a transmission focus, a scan line density, a dynamic range, a brightness gamma curve, or a number of compounds.

* * * * *